(12) United States Patent
Matalon

(10) Patent No.: US 7,807,618 B2
(45) Date of Patent: Oct. 5, 2010

(54) METHODS AND COMPOSITIONS FOR DELIVERING ENZYMES AND NUCLEIC ACID MOLECULES TO BRAIN, BONE AND OTHER TISSUES

(75) Inventor: Reuben Matalon, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 898 days.

(21) Appl. No.: 10/386,144

(22) Filed: Mar. 11, 2003

(65) Prior Publication Data

US 2003/0215432 A1 Nov. 20, 2003

Related U.S. Application Data

(60) Provisional application No. 60/381,934, filed on May 20, 2002.

(51) Int. Cl.
*A01N 37/18* (2006.01)
*A61K 38/00* (2006.01)
*A61K 49/00* (2006.01)

(52) U.S. Cl. .............................. 514/2; 424/9.1; 424/9.2
(58) Field of Classification Search ........................ None
See application file for complete search history.

(56) References Cited

U.S. PATENT DOCUMENTS

| | | | |
|---|---|---|---|
| 4,524,065 | A | 6/1985 | Pinnell |
| 4,568,543 | A | 2/1986 | Borrelli et al. |
| 4,645,668 | A | 2/1987 | Pinnell |
| 4,820,516 | A | 4/1989 | Sawyer et al. |
| 5,116,615 | A | 5/1992 | Gokcen et al. |
| 5,739,118 | A | 4/1998 | Carrano et al. |
| 5,854,046 | A | 12/1998 | Au-Young et al. |
| 6,114,161 | A | 9/2000 | Truog et al. |
| 6,171,575 | B1 | 1/2001 | Okuyama |
| 6,193,963 | B1 | 2/2001 | Stern et al. |
| 6,214,978 | B1 | 4/2001 | Truog et al. |
| 6,258,791 | B1 | 7/2001 | Braun |
| 6,296,847 | B1 | 10/2001 | Gokcen et al. |
| 2003/0170243 | A1 | 9/2003 | Stern et al. |

FOREIGN PATENT DOCUMENTS

| | | |
|---|---|---|
| EP | 0 263 417 | 9/1987 |
| WO | WO 99/29841 | 6/1999 |
| WO | WO 00/52149 | 9/2000 |

OTHER PUBLICATIONS

Dietz and Bahr (2004) Delivery of bioactive molecules into the cell: the Trojan horse approach. Molecular and Cellular Neuroscience 27: 85-131.*
Emerich, DF (2000) Recent efforts to overcome the blood-brain barrier for drug delivery. Expert Opinion on Therapeutic Patents 10(3): 279-287.*
Gao et al. (1997) The therapeutic potentials of neurotrophic factors for diseases of the nervous system. Expert Opinion on Therapeutic Patents 7(4): 325-338.*
Pardridge, WM (1997) Drug delivery to the brain. Journal of Cerebral Blood Flow and Metabolism 17: 713-731.*
Robert et al. "Action of Proteolytic and Glycolytic Enzymes on the Permeability of the Blood-Brain Barrier," *Biomedicine*, 21(l):36-39 (1974).
Dubensky et al., "Direct Transfection of Viral and Plasmid DNA into the Liver or Spleen of Mice," *Proc. Natl. Acad. Sci. U.S.A.*, 81(23):7529-7533 (1984).
Hermann et al., "Gaucher Disease: An Assessment of Skeletal Involvement and Therapeutic Responses to Enzyme Replacement," *Skeletal Radiol.*, 26(12):687-696 (1997).
Fromes et al., "Gene Delivery to the Myocardium by Intrapericardial Injection," *Gene Ther.*, 6(4):683-688 (1999).
Vellodi et al., "Management of Neuropathic Gaucher Disease: A European Consensus," *J. Inherit. Metab. Dis.*, 24(3):319-327 (2001).
Senitz et al., "Intravenous Application of Hylase 'Dessau'—Experimental Studies in Rats. Early Reactions in Plexus Chorioideus and Ependyma," *Exp. Pathol. (Jena)*, 6(1):47-49 (1972).

(Continued)

*Primary Examiner*—Anne-Marie Falk
(74) *Attorney, Agent, or Firm*—Benjamin Aaron Adler

(57) ABSTRACT

Disclosed are methods for delivering an enzyme to a subject's brain or bone. The methods include administering a hyaluronidase to the subject and administering the enzyme to the subject. The hyaluronidase and the enzyme are administered to the subject under conditions effective to deliver the enzyme to the subject's brain or bone. Compositions and kits which include hyaluronidase and an enzyme are also disclosed, as are methods for increasing blood-brain barrier permeability in a subject. Also disclosed are methods, compositions, and kits for delivering genes or other nucleic acid molecules to a subject's brain or bone, as well as methods, compositions, and kits for delivering enzymes to a subject's tissues. The methods, compositions, and kits are disclosed as being useful in treating or preventing a variety of enzyme deficiency diseases, such as those affecting brain and/or bone, e.g., as Canavan's disease, Fabry disease, Gaucher's disease, various forms of mucopolysaccharidosis (e.g., Hurler's syndrome, Scheie syndrome, Hurler-Scheie syndrome, Sanfillippo A syndrome, Morquio A syndrome, Morquio B syndrome, etc.), Niemann-Pick disease, Schindler disease, and Pompe disease.

15 Claims, 3 Drawing Sheets

OTHER PUBLICATIONS

Senitz et al., "Intravenous Application of Hylase 'Dessau'—Experimental Studies in Rats. Effect of Hylase 'Dessau' on the Blood Brain Barrier," *Exp. Pathol. (Jena)*, 7(5):228-233 (1972).

Orkin et al., "Isolation and Characterization of Hyaluronidase from Cultures of Chick Embryo Skin- and Muscle-Derived Fibroblasts," *J. Biol. Chem.*, 255(3):1036-1042 (1980).

Triggs-Raine et al., "Mutations in HYAL1, a Member of a Tandemly Distributed Multigene Family Encoding Disparate Hyaluronidase Activities, Cause a Newly Described Lysosomal Disorder, Mucopolysaccharidosis IX," *Proc. Natl. Acad. Sci. U.S.A.*, 96(11):6296-6300 (1999).

O'Brien, "The Lysosomal Storage Diseases," *Mayo Clinic Proceedings*, 57(3):192-193 (1982).

Yew et al., "Gene Therapy for Lysosomal Storage Disorders," *Current Opinion in Molecular Therapeutics*, 3(4):399-406 (2001).

* cited by examiner

METHODS AND COMPOSITIONS FOR DELIVERING ENZYMES AND NUCLEIC ACID MOLECULES TO BRAIN, BONE AND OTHER TISSUES

The present application claims the benefit of U.S. Provisional Patent Application Ser. No. 60/381,934, filed May 20, 2002, which provisional patent application is hereby incorporated by reference.

FIELD OF THE INVENTION

The present invention is directed to methods for delivering enzymes and nucleic acid molecules to brain and bone.

BACKGROUND OF THE INVENTION

A wide variety of diseases and other conditions which afflict humans are caused by deficiencies in certain enzymes in certain tissues.

Illustratively, Gaucher disease is associated with glucocerebrosidase deficiency and results in brain and bone marrow abnormalities. Hurler's syndrome and Scheie syndrome are associated with α-iduronidase deficiency; the former results in bone, cartilage, and brain abnormalities, while the latter results in corneal clouding and deformed hands. Canavan's disease is associated with aspartoacylase deficiency and results in brain and muscle abnormalities. Fabry disease is associated with α-galactosidase deficiency and results in renal, cardiac, and cerebrovascular abnormalities. Niemann-Pick disease is associated with sphingomyelinase deficiency and results in liver, spleen, lymph node, and bone marrow abnormalities with cerebral involvement in late stage. Schindler disease is associated with α-N-acetylgalactosaminadase deficiency and results in brain abnormalities. Sanfillippo A syndrome is associated with sulfamidase deficiency and results in severe mental retardation and mild skeletal abnormalities. Morquio A and Morquio B syndrome syndromes are, respectively, associated (i) with galactose-4-sulfatase, galactose-6-sulfatase, galactosamine-4-sulfatase, and/or galactosamine-6-sulfatase deficiency and (ii) with β-galactosidase deficiency, and each results in skeletal abnormalities. Pompe disease is associated with α-glucosidase deficiency and results in muscle abnormalities, particularly cardiac muscle abnormalities, as well as brain abnormalities.

A variety of methods have been proposed for treating diseases and other conditions involving enzyme deficiency.

For example, one possible way of treating enzyme deficiency conditions is by enzyme replacement therapy, where exogenous enzyme is delivered to the tissue or tissues where deficiency in the enzyme exists. However, currently used enzyme replacement therapy methods have not been successful when treating diseases and other conditions associated with enzyme deficiencies in the brain or in bone. For example, it has been reported that currently used intravenous methods for enzyme delivery for treating Gaucher disease and for treating syndromes associated with α-iduronidase deficiency (e.g., Hurler's syndrome, Scheie syndrome, and Hurler/Scheie syndrome) are not effective for delivering the necessary enzyme to the brain or to bone (Villodie et al., "Management of Neuropathic Gaucher Disease: A European Consensus," *J. Inherit. Metab. Dis.*, 3:319-327 (2001) and Hermann et al., "Gaucher Disease: An Assessment of Skeletal Involvement and Therapeutic Responses to Enzyme Replacement," *Skeletal Radiol.*, 26(12):687-696 (1977)).

Another possible way of treating enzyme deficiency diseases is by gene therapy by delivering an exogenous gene encoding the deficient enzyme to the tissues where the enzyme is deficient. Once delivered to the desired tissues, the enzyme is produced in situ by expression of the exogenous gene. However, delivery of exogenous genes to the brain and to bone has proven to be problematic. For example, while expression of exogenous genes in brain has previously been achieved in vivo with either viral vectors or cationic liposomes, delivery of cationic liposomes, viral vectors, genes, and other large biologically active materials to the brain generally requires highly invasive routes of administration.

It is believed that the difficulties encountered in delivering enzymes and genes, as well as other large biologically-active materials, to the brain is the result of the inability of such large biologically-active materials to cross the brain capillary wall which forms the blood-brain barrier ("BBB"). The existence of the BBB frequently necessitates administering the large biologically active materials, such as enzymes and exogenous genes, intracerebrally (e.g., via craniotomy). Intracerebral administration requires specialized skills and renders the brain more susceptible to infection.

For all of the above reasons, a need remains for increasing the permeability of the blood-brain barrier, and a need remains for methods of delivering large biologically active materials, such as enzymes and nucleic acid molecules, to the brain and to bone. The present invention is directed, in part, to addressing these needs.

SUMMARY OF THE INVENTION

The present invention relates to a method for delivering an enzyme to a subject's brain. The method includes administering a hyaluronidase to the subject and administering an enzyme to the subject. The hyaluronidase and the enzyme are administered to the subject under conditions effective to deliver the enzyme to the subject's brain.

The present invention relates to a method for delivering a nucleic acid composition to a subject's brain. The method includes administering a hyaluronidase to the subject and administering a nucleic acid composition to the subject. The hyaluronidase and the nucleic acid composition are administered to the subject under conditions effective to deliver the nucleic acid composition to the subject's brain.

The present invention also relates to a method for increasing blood-brain barrier permeability in a subject by administering a hyaluronidase to the subject under conditions effective to increase permeability of the subject's blood-brain barrier.

The present invention also relates to a method for increasing blood-brain barrier permeability in a subject by contacting the subject's blood-brain barrier with a hyaluronidase under conditions effective to increase permeability of the subject's blood-brain barrier.

The present invention also relates to a composition which includes a hyaluronidase and a material selected from the group consisting of (i) an enzyme which is required for a brain's normal biological function and (ii) and a nucleic acid composition. The nucleic acid composition includes a nucleic acid molecule encoding an enzyme which is required for a brain's normal biological function.

The present invention also relates to a kit for delivering a material selected from the group consisting of an enzyme and a nucleic acid composition into a brain. The kit includes a hyaluronidase and a material selected from the group consisting of (i) an enzyme which is required for a brain's normal biological function and (ii) and a nucleic acid composition.

The nucleic acid composition includes a nucleic acid molecule encoding an enzyme which is required for a brain's normal biological function.

The present invention also relates to a method for delivering a material selected from the group consisting of an enzyme and a nucleic acid composition to a subject's bone. The method includes administering a hyaluronidase to the subject and administering a material selected from the group consisting of an enzyme and a nucleic acid composition to the subject. The hyaluronidase and the material are administered to the subject under conditions effective to deliver the material to the subject's bone.

The present invention also relates to a composition which includes a hyaluronidase and a material selected from the group consisting of (i) an enzyme which is required for a bone's normal biological function and (ii) and a nucleic acid composition. The nucleic acid composition includes a nucleic acid molecule encoding an enzyme which is required for a bone's normal biological function.

The present invention also relates to a kit for delivering a material selected from the group consisting of an enzyme and a nucleic acid composition into a bone. The kit includes a hyaluronidase and a material selected from the group consisting of (i) an enzyme which is required for a bone's normal biological function and (ii) and a nucleic acid composition. The nucleic acid composition includes a nucleic acid molecule encoding an enzyme which is required for a bone's normal biological function.

The present invention also relates to a method for delivering an enzyme to a subject's tissue. The method includes administering a hyaluronidase to the subject and administering an enzyme to the subject. The hyaluronidase and the enzyme are administered to the subject under conditions effective to deliver the material to the subject's tissue.

The present invention also relates to a composition which includes a hyaluronidase and an enzyme which is required for normal biological function of a tissue.

The present invention also relates to a kit for delivering an enzyme into a tissue. The kit includes a hyaluronidase and an enzyme which is required for normal biological function of a tissue.

BRIEF DESCRIPTION OF THE DRAWINGS

FIG. 1A shows the absence of green fluorescence in a mouse to which neither FITC-Dextran nor hyaluronidase was administered. FIG. 1B shows the absence of green fluorescence in a mouse to which no hyaluronidase was administered but to which FITC-Dextran was administered. FIG. 1C shows the green fluorescence in the brain, bone, kidney and liver of a mouse to which hyaluronidase was administered followed by FITC-Dextran administration.

DETAILED DESCRIPTION OF THE INVENTION

Figure 1A:
FIGS. 1A-1C are gray scale images of sagittal sections of mice viewed under UV light for fluorescein isothiocyanate ("FITC") fluorescence at 400 nm wavelength. The images were heavily weighted for green so that green fluorescence appears as bright areas in the gray scale images.

One aspect of the present invention relates to a method for delivering a material selected from the group consisting of an enzyme and a nucleic acid composition to a subject's brain. The method includes administering a hyaluronidase to the subject and administering a material selected from the group consisting of an enzyme and a nucleic acid composition to the subject. The hyaluronidase and the material are administered to the subject under conditions effective to deliver the material to the subject's brain.

As used herein, "subject" is meant to refer to any organism having a brain and a circulatory system separated by a blood-brain barrier. Illustratively, subjects are meant to include mammals, such as humans and other primates as well as rats, mice, and other rodents. As further illustration, subjects are meant to include humans suffering from a condition involving deficiency of an enzyme in his or her brain; humans having a deficiency, within his or her brain, of an enzyme selected from the group consisting of aspartoacylase, α-galactosidase, glucocerebrosidase, sulfamidase, sphingomyelinase, α-N-acetylgalactosaminadase, and combinations thereof; and/or humans suffering from Canavan's disease, Fabry disease, Gaucher's disease, mucopolysaccharidosis (e.g., Sanfillippo A syndrome, Hurler's syndrome, Hurler-Sheie syndrome, etc.), Niemann-Pick disease, Schindler disease, Pompe disease or combinations thereof.

As used herein, "hyaluronidase" is meant to refer to a substance which hydrolyze hyaluronic acid. Various hyaluronidases suitable for use in the practice of the present invention are described in Kreil, Hyaluronidases—A Group of Neglected Enzymes, *Protein Sci.*, 4(9):1666-1669 (1995), which is hereby incorporated by reference. The hyaluronidase can be a hyaluronidase which is derived from a mammalian, reptilian, or hymenopteran hyaluronate glycanohydrolase, from a hyaluronate glycanohydrolase from the salivary gland of the leech, or from a bacterial (e.g., streptococcal, pneumococcal, or clostridial) hyaluronate lyase. Other hyaluronidase, such as bovine testicular hyaluronidase, are also suitable. "Hyaluronidase", as used herein, is also meant to include a substance which exhibits a degree of homology of at least about 70% (e.g., of at least about 80%, of at least about 90%, of at least about 95%, and/or of at least 97%, with the amino acid sequence of a naturally-occurring hyaluronidase or a functional fragment of such a naturally-occurring hyaluronidase, so long as hyaluronidase activity is conserved. This enzymic activity can be assessed by conventional techniques, such as those described in Hynes et al., "Assays for Hyaluronidase Activity," *Methods Enzymol.*, 235:606-616 (1994) and/or Bailey et al., "Optimization of the USP Assay for Hyaluronidase, *J. Pharm. Biomed. Anal.*, 11 (4-5):285-292 (1993), which are hereby incorporated by reference. The hyaluronidase used in the practice of the present invention can be obtained commercially, preferably in a grade which is acceptable from the pharmaceutical point of view. Alternatively, the hyaluronidase can be isolated form natural materials by methods well known to those skilled in the art, or it can be produced recombinantly using conventional techniques known to those skilled in the art.

Administration of the hyaluronidase to the subject can be carried out by any conventional method. Illustratively, the hyaluronidase can be administered by dissolving or suspending the hyaluronidase in a suitable carrier and administering the resulting solution or suspension enterally or parenterally (e.g., intraventricularly, intracerebrally, intramuscularly, intravenously, intraperitoneally, rectally, subcutaneously, etc.) to the subject. Alternatively, it is also possible to administer the hyaluronidase to the subject by administering a substance which produces hyaluronidase in the subject. For example, a nucleic acid sequence encoding a hyaluronidase can be placed in a suitable expression vector (e.g., together with or separate from the expression vector discussed below in connection with the nucleic acid composition (discussed further below)) under the control of elements which are suitable for expressing the hyaluronidase in the subject.

As indicated above, the method of the present invention further includes administering a material selected from the group consisting of an enzyme and a nucleic acid composition to the subject.

"Enzyme", as used herein, is meant to refer to polypeptides which catalyze or are otherwise involved in biological processes. Where enzymes are employed, the choice of enzyme will typically be dictated by the disease or other condition from which the subject suffers. Suitable enzymes include those which are required for a brain's normal biological function, such as aspartoacylase, α-galactosidase, glucocerebrosidase, sulfamidase, sphingomyelinase, and α-N-acetylgalactosaminadase. It is to be understood, that the enzyme employed in the practice of the present invention can be one which is also required for normal biological function in non-brain tissue, or it can be one which is not required for normal biological function in non-brain tissue. Illustratively, the enzyme employed in the practice of the present invention can be one which is also required for normal biological function in brain tissue, bone tissue, and other (i.e., non-brain, non-bone) tissues; or it can be one which is required for normal biological function in brain tissue and in bone tissue, but which is not required for normal biological function in other (i.e., non-brain, non-bone) tissues.

"Nucleic acid composition", as used herein is meant to refer to compositions which include, at a minimum, one or more nucleic acid molecules. Where nucleic acid compositions are employed, the choice of nucleic acid molecule contained therein will typically be dictated by the disease or other condition from which the subject suffers. For example, where the subject suffers from a deficiency in an enzyme which is required for a brain's normal biological function, the nucleic acid molecule can be one which encodes for or otherwise promotes the in vivo production of the deficient enzyme. Illustratively, the nucleic acid molecule can be one which encodes for aspartoacylase, α-galactosidase, glucocerebrosidase, sulfamidase, sphingomyelinase, and/or α-N-acetylgalactosaminadase. It is to be understood, that the enzyme for which the nucleic acid molecule encodes can be one which is also required for normal biological function in non-brain tissue, or it can be one which is not required for normal biological function in non-brain tissue. Illustratively, the enzyme for which the nucleic acid molecule encodes can be one which is also required for normal biological function in brain tissue, bone tissue, and other (i.e., non-brain, non-bone) tissues; or the enzyme for which the nucleic acid molecule encodes can be one which is required for normal biological function in brain tissue and in bone tissue, but which is not required for normal biological function in other (i.e., non-brain, non-bone) tissues.

Within the context of the present invention, the nucleic acid molecule used in the nucleic acid composition can be a sense or antisense oligonucleotide, a ribonucleic acid, or deoxyribonucleic acid. In brief, "sense" refers to a nucleic acid which possesses a sequence which is homologous with or identical to a target sequence, whereas "antisense" refers to a nucleic acid which possesses a sequence which is homologous with or identical to a sequence which is complementary to a target sequence. The nucleic acid molecule will typically contain a gene of interest (e.g., a gene which encodes for an enzyme which is required for a brain's normal biological function) and elements which enable the gene to be expressed in a cell or a host organism. The nucleic acid composition further includes a vector, such as a plasmid, a viral vector, or other suitable expression vector. Illustrative viral vectors include those derived from an adenovirus, retrovirus, poxvirus (e.g., derived from vaccinia virus or an MVA virus), herpes virus, adenovirus-associated virus, and the like. The nucleic acid of interest is transported by means of an infectious viral particle or in the form of a synthetic vector (cationic lipid, liposome, cationic polymer, etc.) or an engineered cell (cell which is transfected or transduced with the said nucleic acid) or non-engineered cell (which naturally contains the said nucleic acid).

In the case where the nucleic acid composition contains a nucleic acid molecule and a plasmid (e.g., where the nucleic acid molecule is in plasmid DNA form), the choice of plasmids which can be used within the context of the present invention is vast. They can be of any origin whatsoever (prokaryotic or eukaryotic), or they can be formed by assembling various elements. While a large number of suitable plasmids are commercially available, other plasmids can be prepared using genetic manipulation techniques, for example, as described in Maniatis et al., *Laboratory Manual*, Cold Spring Harbor, N.Y.: Cold Spring Harbor Laboratory Press (1989) ("Maniatis"), which is hereby incorporated by reference. The plasmid can be a cloning or expression vector which is derived, for example, from pBR322 (Gibco BRL), pUC (Gibco BRL), pBluescript (Stratagene), pREP4, pCEP4 (Invitrogen) or else p Poly (Lathe et al., "Plasmid and Bacteriophage Vectors for Excision of Intact Inserts," *Gene*, 57 (2-3):193-201 (1987), which is hereby incorporated by reference. Plasmid DNA can be amplified and purified in accordance with the general practices of the art. For example, in one technique, the plasmid is introduced into producer cells (for example *Escherichia coli*); these cells are then cultured under appropriate conditions (readily established by the skilled person on the basis of general knowledge in the field and of the selection system carried by the plasmid); and plasmid DNA is then recovered and optionally purified using the conventional techniques, for example, as described in Maniatis, which is hereby incorporated by reference.

In the case where the nucleic acid composition contains a nucleic acid molecule and a viral vector, the nucleic acid molecule of interest can be carried by any suitable viral vector, such as an adenoviral vector which is defective for replication (unable to replicate autonomously in a host cell). Methods for making and using adenoviruses are described, for example, in Graham et al, pp. 109-128 in Murey, ed., *Molecular Biology*, vol. 7, Totowa, N.J.: The Human Press, Inc. (1991), which is hereby incorporated by reference. Examples of suitable adenoviral vectors which are useful within the context of the present invention include those which are derived from the genome of an adenovirus; which include at least the inverted terminal repeats ("ITRs") and an encapsidation sequence; and which lack all or part of the E1 adenoviral region. In addition, the adenoviral vector can lack all or part of the E3 adenoviral region, for example, as in the case where the adenoviral vector lacks part of the E3 adenoviral region but retains that part of the E3 region which encodes polypeptides, such as the glycoprotein gp19 k (Gooding et al., "Molecular Mechanisms by Which Adenoviruses Counteract Antiviral Immune Defenses," *Critical Review of Immunology*, 10(1):53-71 (1990), which is hereby incorporated by reference) or other polypeptides which make it possible for the adenoviral vector to escape the immune system of the host. Furthermore, the adenoviral vector can contain additional deletions or mutations which affect, in particular, all or part of one or more regions selected from the E2, E4, L1, L2, L3, L4 and L5 regions (see, for example, international application WO 94/28152, which is hereby incorporated by reference). In order to illustrate this point, mention may be made of the temperature-sensitive mutation which affects the DNA-binding protein ("DBP") gene of the E2 A region (Ensinger et al., "Selection and Preliminary Characterization of Temperature-sensitive Mutants of Type 5 Adenovirus," *J. Virol.*, 10: 328-339 (1972), which is hereby incorporated by reference). Another mutation which may be mentioned in this regard involves the deletion of the E4 region with the exception of the sequences which encode open reading frames ("ORFs") 6 and 7 (Ketner et al., "Complementation of Adenovirus E4 Mutants by Transient Expression of E4 cDNA and Deletion Plasmids," *Nucleic Acids Res.*, 17(8): 3037-3048 (1989), which is hereby incorporated by reference). The nucleic acid molecules of interest (e.g., a gene which encodes for an enzyme which is required for a brain's normal biological function) is typically inserted into the vector in place of the deleted adenoviral regions, in particular the E1 region. When several genes of interest are used, they can be inserted at the same site or at different sites in the viral genome and can be under the control of the same regulatory elements or of independent elements and, where appropriate, some of them can be in the opposite orientation to the others, for example, so as to reduce the phenomena of interference at the level of their expression. The genome of the recombinant adenoviral vector can be prepared by molecular biology techniques or by homologous recombination, for example, as described in WO 96/17070, which is hereby incorporated by reference.

The adenoviral vectors which are useful in the context of the present invention can be propagated in a complementing cell line which is able to supply the defective function(s), for example, in order to produce peptides which are required for forming the infectious viral particles. Illustratively, use can be made of cell line 293 for complementing the E1 function (Graham et al., "Characteristics of a Human Cell Line Transformed by DNA from Human Adenovirus Type 5," *J. Gen. Virol.*, 36(1):59-74 (1977), which is hereby incorporated by reference), or use can be made of the cell lines described in international application WO 97/04119 (which is hereby incorporated by reference) for effecting a double complementation. Additionally or alternatively, a helper virus can be used to complement defective functions. The viral particles which are produced are recovered from the cell culture and optionally purified using conventional techniques of the art (e.g., cesium chloride gradient, chromatography, etc.).

Adenoviral vectors suitable for use within the context of the present invention can be derived from the genome of an adenovirus of human, canine, avian, bovine, murine, ovine, porcine, or simian origin, or it can be derived from a hybrid which comprises adenoviral genome fragments of different origins. Mention may be made, for example, of the CAV-1 or CAV-2 adenoviruses of canine origin, of DAV adenoviruses of avian origin, and of type 3 Bad adenoviruses of bovine origin. These and other suitable adenoviruses are described in Zakharchuk et al., "Physical Mapping and Homology Studies of Egg Drop Syndrome (EDS-76) Adenovirus DNA," *Arch. Virol.*, 128 (1-2):171-176 (1993); Spibey et al., "Molecular Cloning and Restriction Endonuclease Mapping of Two Strains of Canine Adenovirus Type 2," *J. Gen. Virol.*, 70 (Pt 1):165-172 (1989); Jouvenne et al., Cloning, Physical Mapping and Cross-hybridization of the Canine Adenovirus Types 1 and 2 Genomes," *Gene*, 60(1):21-28 (1987); and Mittal et al., "Development of a Bovine Adenovirus Type 3-based Expression Vector," *J. Gen. Virol.*, 76 (Pt 1):93-102 (1995); which are hereby incorporated by reference. Still other adenoviral vectors suitable for use within the context of the present invention include adenoviral vectors of human origin, such as those derived from a serotype C adenovirus, in particular a type 2 or type 5 adenovirus.

As indicated above, the nucleic acid molecule of interest can encode an antisense RNA and/or an mRNA which will then be translated into a polypeptide of therapeutic interest (e.g., an enzyme which is required for a brain's normal biological function). Alternatively, the nucleic acid molecule can be of a genomic type, a complementary DNA ("cDNA") type, or a mixed type (e.g., a minigene from which at least one intron has been deleted), and can be homologous or heterologous in relation to the host cell. The polypeptide (e.g., enzyme) which it encodes can correspond to all or part of a protein as is found in nature (native or truncated protein) or a mutant which exhibits improved and/or modified biological properties. The polypeptide (e.g., the enzyme) can also be a chimeric polypeptide (e.g., a chimeric enzyme) which is the result of fusing sequences of varied origin. The nucleic acid molecule of interest can be obtained by chemical synthesis or by cloning (e.g., by screening DNA libraries using suitable probes, PCR, etc.), and it can optionally modified using conventional techniques of molecular biology.

Administration of the enzyme or nucleic acid composition to the subject can be carried out by any conventional method. For example, the enzyme or nucleic acid composition can be administered by dissolving or suspending the enzyme or nucleic acid composition (as the case may be) in a suitable carrier and administering the resulting solution or suspension enterally or parenterally (e.g., intraventricularly, intramuscularly, intracerebrally, intravenously, intraperitoneally, rectally, subcutaneously, etc.) to the subject.

The enzyme or nucleic acid composition can be administered concurrently with the hyaluronidase, either separately (e.g., in two separate suspensions or solutions, one containing the hyaluronidase and the other containing the enzyme or nucleic acid composition) or together (e.g., in a single solution or suspension containing both the hyaluronidase and the enzyme or nucleic acid composition).

Alternatively, the hyaluronidase can be administered after the time at which the enzyme or nucleic acid composition is administered. Of course, optimal relative administration times will depend on the rates of metabolism and/or excretion of the hyaluronidase and of the enzyme or nucleic acid composition. For example, in the case where the hyaluronidase is administered after the time at which the enzyme or nucleic acid composition is administered, it is generally desirable to administer the hyaluronidase prior to the time at which 50% (e.g., prior to the time at which 20%, 10%, 5%) of the enzyme or nucleic acid composition is metabolized or excreted by the subject. Illustratively, in the case where the hyaluronidase is administered after the time at which the enzyme or nucleic acid composition is administered, the time between administration of the hyaluronidase and administration of the enzyme or nucleic acid composition can be less than about 1 day (e.g., less than about 12 hours, less than about 6 hours, less than about 5 hours, less than about 4 hours, less than about 3 hours, less than about 2 hours, less than about 1 hour, less than about 30 minutes, less than about 15 minutes, less than about 10 minutes, less than about 5 minutes, and/or less than about 1 minute.

Alternatively, the hyaluronidase can be administered before the time at which the enzyme or nucleic acid composition is administered. Of course, optimal relative administration times will depend on the rates of metabolism and/or excretion of the hyaluronidase and of the enzyme or nucleic acid composition. For example, in the case where the hyaluronidase is administered before the time at which the enzyme or nucleic acid composition is administered, it is generally desirable to administer the enzyme or nucleic acid composition prior to the time at which 50% (e.g., prior to the time at which 20%, 10%, 5%) of the hyaluronidase is metabolized or excreted by the subject. Illustratively, in the case where the hyaluronidase is administered before the time at which the enzyme or nucleic acid composition is administered, the time between administration of the hyaluronidase and administration of the enzyme or nucleic acid composition can be less than about 1 day (e.g., less than about 12 hours, less than about 6 hours, less than about 5 hours, less than about 4 hours, less than about 3 hours, less than about 2 hours, less than about 1 hour, less than about 30 minutes, less than about 15 minutes, less than about 10 minutes, less than about 5 minutes, and/or less than about 1 minute.

Either or both of the hyaluronidase and the enzyme or nucleic acid composition can be administered separately in single doses or in multiple discrete doses, or continuously over a suitable period of time. Single and multiple dose administration can be carried out for example enterally (e.g., in tablet form) or parenterally (e.g., by intravenous methods). Continuous administration can be carried out parenterally (e.g., by intravenous methods). Illustratively, in the case where the hyaluronidase is administered in multiple discrete doses or continuously before the time at which the enzyme or nucleic acid composition is administered, hyaluronidase administration can commence less than 6 days (e.g., less than 5 days, less than 4 days, less than 3 days, less than 2 days, less than 1 day, less than 12 hours, less than 6 hours, less than 3 hours, and/or less than 1 hour) prior to the time at which the enzyme or nucleic acid composition is to be administered to the subject. Additionally or alternatively, the hyaluronidase can be administered to the subject in a single dose, in multiple doses, or continuously within a 72-hour period (e.g., within a 48-hour period, within a 24-hour period, and/or 12-hour period) immediately preceding administration of the enzyme or nucleic acid composition to the subject.

As indicated above, the hyaluronidase and the enzyme or nucleic acid composition are administered to the subject under conditions effective to deliver the enzyme or nucleic acid composition to the subject's brain. As one skilled in the art will recognize, the hyaluronidase and/or enzyme or nucleic acid composition may be made up, together or separately, in any suitable form appropriate for the desired use and route of administration. Examples of suitable dosage forms include oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

In addition to the above, generally non-active components of the above-described formulations, these formulations can include other active materials, particularly, actives which have been identified as useful in the treatment of conditions involving deficiencies in brain enzymes or symptoms associated therewith. These actives can be broad-based therapeutic agents, such that they also are useful in treating or alleviating symptoms associated with enzyme deficiencies in tissues other than brain tissue or they may be more specific, for example, in the case where the other active is useful in treating or alleviating symptoms associated with enzyme deficiencies in tissues but not useful in treating or alleviating symptoms associated with enzyme deficiencies in tissues other than brain tissue.

It will be appreciated that the actual preferred amount of hyaluronidase and the actual preferred amount of enzyme or nucleic acid composition to be administered according to the present invention will vary according to the particular compound, the particular composition formulated, and the mode of administration. Many factors that may modify the action of the hyaluronidase and/or of the enzyme or nucleic acid composition (e.g., body weight, sex, diet, time of administration, route of administration, rate of excretion, condition of the subject, drug combinations, and reaction sensitivities and severities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

The present invention also relates to methods for increasing blood-brain barrier permeability in a subject. In one such method, hyaluronidase is administered to the subject under conditions effective to increase permeability of the subject's blood-brain barrier. In another such method, the subject's blood-brain barrier is contacted with a hyaluronidase. "Blood-brain barrier permeability", as used herein, refers to the degree to which large molecules (e.g., having a molecular weight of at least 5 kDa, such as at least about 10 kDa, at least about 20 kDa, at least about 30 kDa, at least about 40 kDa, at least about 50 kDa, at least about 60 kDa, at least about 70 kDa, about 66 kDa, etc.) crosses the blood-brain barrier. "Increase", as used in this context, is meant to include any measurable increase in blood-brain barrier permeability, such as, for example, an increase of greater than about 5% (e.g., greater than about 10%, greater than about 15%, greater than about 20%, greater than about 40%, greater than about 60%, greater than about 80%, greater than about 100%, and/or greater than about 150%). Methods, dosage forms, and routes of administration suitable for use in the practice of this method of the present invention include those set forth above in connection with methods for delivering enzymes and nucleic acid compositions to a subject's brain. Illustratively, the subject's blood-brain barrier can be contacted with the hyaluronidase over a period of time not exceeding about 6 days (such as over a period of time not exceeding 5 days, not exceeding 4 days, not exceeding 3 days, not exceeding 2 days, not exceeding 1 day, not exceeding 12 hours, and/or not exceeding 3 hours) and/or over a period of time from about 5 minutes to about 3 hours, such as over a period of time from about 15 minutes to about 1 hour. Suitable subjects, include, for example, rats, mice, and humans, such as humans suffering from a condition involving deficiency of an enzyme in his or her brain; humans having a deficiency, within his or her brain, of an enzyme selected from the group consisting of aspartoacylase, α-galactosidase, glucocerebrosidase, sulfamidase, sphingomyelinase, α-N-acetylgalactosaminadase, and combinations thereof; and/or humans suffering from Canavan's disease, Fabry disease, Gaucher's disease, mucopolysaccharidosis (e.g., Sanfilippo A syndrome, Hurler's syndrome, Hurler-Sheie syndrome, etc.), Niemann-Pick disease, Schindler disease, Pompe disease or combinations thereof.

The present invention further relates to compositions and kits which include, at a minimum, a hyaluronidase and a material selected from the group consisting of (i) an enzyme which is required for a brain's normal biological function and (ii) and a nucleic acid composition comprising a nucleic acid molecule encoding an enzyme which is required for a brain's normal biological function. Suitable enzymes for use in the composition of the present invention include those which are required for a brain's normal biological function but which are not required for normal biological function in non-brain tissues. Examples of suitable enzymes include aspartoacylase, α-galactosidase, glucocerebrosidase, sulfamidase, sphingomyelinase, and α-N-acetylgalactosaminadase. Suitable nucleic acid compositions include those which have been described in detail above in connection with methods for delivering enzymes and nucleic acid compositions to a subject's brain. The compositions and kits of this aspect of the present invention can also include other active ingredients as well as non-active ingredients, such as those set forth above in connection with formulations suitable for use in methods for delivering enzymes and nucleic acid compositions to a subject's brain.

The methods, compositions, and kits of the present invention can be used in a variety of ways. For example, delivery of polypeptides (e.g., enzymes, antibodies, and the like) can be useful in the diagnosis, prevention, and/or treatment of various brain diseases, syndromes, disorders, and conditions. For example, delivery of polypeptides (e.g., enzymes, antibodies, and the like) can be useful in the treatment of various brain diseases, disorders, and conditions involving deficiency of an enzyme, such as aspartoacylase (Canavan's disease), α-galactosidase (Fabry disease), glucocerebrosidase (Gaucher's disease), sulfamidase (Sanfilippo A syndrome), α-iduronidase (Hurler's syndrome, Hurler-Sheie syndrome, etc.), sphingomyelinase (Niemann-Pick disease), α-N-acetylgalactosaminadase (Schindler disease), and α-glucosidase (Pompe disease), either by directly introducing the deficient enzyme into the brain (enzyme replacement therapy) or by introducing a gene into the brain under conditions effective for the gene to express the deficient enzyme (gene therapy). However, as one skilled in the art will recognize, the ability to increase the permeability of the blood-brain barrier afforded by the present invention has wider application than simply therapeutic and preventative delivery of enzymes and genes to the brain. For example, using the methods of the present invention, blood-brain barrier permeability can be increased so as to facilitate the delivery of antibodies labeled with, e.g., fluorescent dyes to the brain for the study of brain function.

Another aspect of the present invention relates to a method for delivering a material selected from the group consisting of an enzyme and a nucleic acid composition to a subject's bone. The method includes administering a hyaluronidase to the subject and administering a material selected from the group consisting of an enzyme and a nucleic acid composition to the subject. The hyaluronidase and the material are administered to the subject under conditions effective to deliver the material to the subject's bone.

As used herein, "subject" is meant to refer to any organism having a skeleton. Illustratively, subjects are meant to include mammals, such as humans and other primates as well as rats, mice, and other rodents. As further illustration, subjects are meant to include humans suffering from a condition involving deficiency of an enzyme in his or her bone; humans having a deficiency, within his or her bone, of an enzyme selected from the group consisting of glucocerebrosidase, α-iduronidase, sulfamidase, galactose-4-sulfatase, galactose-6-sulfatase, galactosamine-4-sulfatase, galactosamine-6-sulfatase, β-galactosidase, sphingomyelinase, and combinations thereof; and/or humans suffering from Gaucher's disease, mucopolysaccharidosis (e.g., Hurler's syndrome, Scheie syndrome, Hurler-Scheie syndrome, Sanfilippo A syndrome, Morquio A syndrome, Morquio B syndrome, etc.), Niemann-Pick disease, or combinations thereof.

As used herein, "bone" is meant to refer to calcified bone, uncalcified bone (e.g., cartilage), bone marrow, and other components of the skeletal system.

As used herein, "hyaluronidase" is meant to refer to a substance which hydrolyze hyaluronic acid. Hyaluronidases suitable for use in the practice of the present invention include those described hereinabove.

Administration of the hyaluronidase to the subject can be carried out by any conventional method. Illustratively, the hyaluronidase can be administered by dissolving or suspending the hyaluronidase in a suitable carrier and administering the resulting solution or suspension enterally or parenterally (e.g., intraventricularly, intramuscularly, intravenously, intraperitoneally, rectally, subcutaneously, etc.) to the subject. Alternatively, it is also possible to administer the hyaluronidase to the subject by administering a substance which produces hyaluronidase in the subject. For example, a nucleic acid sequence encoding a hyaluronidase can be placed in a suitable expression vector (e.g., together with or separate from the expression vector discussed below in connection with the nucleic acid composition (discussed further below)) under the control of elements which are suitable for expressing the hyaluronidase in the subject.

As indicated above, the method of the present invention further includes administering a material selected from the group consisting of an enzyme and a nucleic acid composition to the subject.

"Enzyme", as used herein, is meant to refer to polypeptides which catalyze or are otherwise involved in biological processes. Where enzymes are employed, the choice of enzyme will typically be dictated by the disease or other condition from which the subject suffers. Enzymes suitable for use in this aspect of the present invention include those which are required for a bone's normal biological function, such as glucocerebrosidase, α-iduronidase, sulfamidase, galactose-4-sulfatase, galactose-6-sulfatase, galactosamine-4-sulfatase, galactosamine-6-sulfatase, β-galactosidase, and sphingomyelinase. It is to be understood, that the enzyme employed in the practice of the present invention can be one which is also required for normal biological function in non-bone tissue, or it can be one which is not required for normal biological function in non-bone tissue. Illustratively, the enzyme employed in the practice of the present invention can be one which is also required for normal biological function in bone tissue, brain tissue, and other (i.e., non-bone, non-brain) tissues; or it can be one which is required for normal biological function in bone tissue and in brain tissue, but which is not required for normal biological function in other (i.e., non-bone, non-brain) tissues.

"Nucleic acid composition", as used herein is meant to refer to compositions which include, at a minimum, one or more nucleic acid molecules. Where nucleic acid compositions are employed, the choice of nucleic acid molecule contained therein will typically be dictated by the disease or other condition from which the subject suffers. For example, where the subject suffers from a deficiency in an enzyme which is required for a bone's normal biological function, the nucleic acid molecule can be one which encodes for or otherwise promotes the in vivo production of the deficient enzyme. Illustratively, the nucleic acid molecule can be one which encodes for glucocerebrosidase, α-iduronidase, sulfamidase, galactose-4-sulfatase, galactose-6-sulfatase, galactosamine-4-sulfatase, galactosamine-6-sulfatase, β-galactosidase, and/or sphingomyelinase. It is to be understood, that the enzyme for which the nucleic acid molecule encodes can be one which is also required for normal biological function in non-bone tissue, or it can be one which is not required for normal biological function in non-bone tissue. Illustratively, the enzyme for which the nucleic acid molecule encodes can be one which is also required for normal biological function in bone tissue, brain tissue, and other (i.e., non-bone, non-brain) tissues; or the enzyme for which the nucleic acid molecule encodes can be one which is required for normal biological function in bone tissue and in brain tissue, but which is not required for normal biological function in other (i.e., non-bone, non-brain) tissues.

Within the context of the present invention, the nucleic acid molecule used in the nucleic acid composition can be a sense or antisense oligonucleotide, a ribonucleic acid, or deoxyribonucleic acid, as described above. The nucleic acid molecule will typically contain a gene of interest (e.g., a gene which encodes for an enzyme which is required for a bone's normal biological function) and elements which enable the gene to be expressed in a cell or a host organism. The nucleic acid composition further includes a vector, such as a plasmid, a viral vector, or other suitable expression vector, suitable examples of which are discussed above.

As indicated above, the nucleic acid molecule of interest can encode an antisense RNA and/or an mRNA which will then be translated into a polypeptide of therapeutic interest (e.g., an enzyme which is required for a bone's normal biological function). Alternatively, the nucleic acid molecule can be of a genomic type, a complementary DNA ("cDNA") type, or a mixed type (e.g., a minigene from which at least one intron has been deleted), and can be homologous or heterologous in relation to the host cell. The polypeptide (e.g., enzyme) which it encodes can correspond to all or part of a protein as is found in nature (native or truncated protein) or a mutant which exhibits improved and/or modified biological properties. The polypeptide (e.g., the enzyme) can also be a chimeric polypeptide (e.g., a chimeric enzyme) which is the result of fusing sequences of varied origin. The nucleic acid molecule of interest can be obtained by chemical synthesis or by cloning (e.g., by screening DNA libraries using suitable probes, PCR, etc.), and it can optionally modified using conventional techniques of molecular biology.

Administration of the enzyme or nucleic acid composition to the subject can be carried out by any conventional method. For example, the enzyme or nucleic acid composition can be administered by dissolving or suspending the enzyme or nucleic acid composition (as the case may be) in a suitable carrier and administering the resulting solution or suspension enterally or parenterally (e.g., intraventricularly, intramuscularly, intravenously, intraperitoneally, rectally, subcutaneously, etc.) to the subject.

The enzyme or nucleic acid composition can be administered concurrently with the hyaluronidase, either separately (e.g., in two separate suspensions or solutions, one containing the hyaluronidase and the other containing the enzyme or nucleic acid composition). Alternatively, the hyaluronidase can be administered before or after the time at which the enzyme or nucleic acid composition is administered, as described in greater detail hereinabove.

As indicated above, the hyaluronidase and the enzyme or nucleic acid composition are administered to the subject under conditions effective to deliver the enzyme or nucleic acid composition to the subject's bone. As one skilled in the art will recognize, the hyaluronidase and/or enzyme or nucleic acid composition may be made up, together or separately, in any suitable form appropriate for the desired use and route of administration. Examples of suitable dosage forms include oral, parenteral, or topical dosage forms and include all of the dosage forms and formulations described hereinabove. In addition to the above, generally non-active components of the above-described formulations these formulations can include other active materials, particularly, actives which have been identified as useful in the treatment of conditions involving deficiencies in bone enzymes or symptoms associated therewith. These actives can be broad-based therapeutic agents, such that they also are useful in treating or alleviating symptoms associated with enzyme deficiencies in tissues other than bone tissue or they may be more specific, for example, in the case where the other active is useful treating or alleviating symptoms associated with enzyme deficiencies in tissues but not useful treating or alleviating symptoms associated with enzyme deficiencies in tissues other than bone tissue.

It will be appreciated that the actual preferred amount of hyaluronidase and the actual preferred amount of enzyme or nucleic acid composition to be administered according to the present invention will vary according to the particular compound, the particular composition formulated, and the mode of administration. Many factors that may modify the action of the hyaluronidase and/or of the enzyme or nucleic acid composition (e.g., body weight, sex, diet, time of administration, route of administration, rate of excretion, condition of the subject, drug combinations, and reaction sensitivities and severities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

The present invention further relates to compositions and kits which include, at a minimum, a hyaluronidase and a material selected from the group consisting of (i) an enzyme which is required for a bone's normal biological function and (ii) and a nucleic acid composition comprising a nucleic acid molecule encoding an enzyme which is required for a bone's normal biological function. Suitable enzymes for use in the composition of the present invention include those which are required for a bone's normal biological function but which are not required for normal biological function in non-bone tissues. Examples of suitable enzymes include glucocerebrosidase, α-iduronidase, sulfamidase, galactose-4-sulfatase, galactose-6-sulfatase, galactosamine-4-sulfatase, galactosamine-6-sulfatase, β-galactosidase, and sphingomyelinase. Suitable nucleic acid compositions include those which have been described in detail above in connection with methods for delivering enzymes and nucleic acid compositions to a subject's bone. The compositions and kits of this aspect of the present invention can also include other active ingredients as well as non-active ingredients, such as those set forth above in connection with formulations suitable for use in methods for delivering enzymes and nucleic acid compositions to a subject's bone.

The methods, compositions, and kits of the present invention can be used in a variety of ways. For example, delivery of polypeptides (e.g., enzymes, antibodies, and the like) can be useful in the diagnosis, prevention, and/or treatment of various bone diseases, syndromes, disorders, and conditions. For example, delivery of polypeptides (e.g., enzymes, antibodies, and the like) can be useful in the treatment of various bone diseases, disorders, and conditions involving deficiency of an enzyme, such as glucocerebrosidase (Gaucher's disease), α-iduronidase (certain forms of mucopolysaccharidosis, such as Hurler's syndrome, Hurler-Scheie syndrome, Scheie syndrome, etc.), sulfamidase (certain other forms of mucopolysaccharidosis, such as Sanfillippo A syndrome), galactose-4-sulfatase, galactose-6-sulfatase, galactosamine-4-sulfatase, galactosamine-6-sulfatase (certain other forms of mucopolysaccharidosis, such as Morquio A syndrome), β-galactosidase (certain other forms of mucopolysaccharidosis, such as Morquio B syndrome), and sphingomyelinase (Niemann-Pick disease), either by directly introducing the deficient enzyme into the bone (enzyme replacement therapy) or by introducing a gene into the bone under conditions effective for the gene to express the deficient enzyme (gene therapy). However, as one skilled in the art will recognize, the ability to deliver large biologically active materials into bone afforded by the present invention has wider application than simply therapeutic and preventative delivery of enzymes and genes to bone. For example, using the methods of the present invention, delivery of antibodies labeled with, e.g., fluorescent dyes into bone can be improved for the study of bone diseases.

Another aspect of the present invention relates to a method for delivering an enzyme to a subject's tissue. The method includes administering a hyaluronidase to the subject and administering an enzyme to the subject. The hyaluronidase and the enzyme are administered to the subject under conditions effective to deliver the material to the subject's tissue.

As used in this context, "subject" is meant to refer to any organism. Illustratively, subjects are meant to include mammals, such as humans and other primates as well as rats, mice, and other rodents. As further illustration, subjects are meant to include humans suffering from a condition involving deficiency of an enzyme in one or more tissues, such as bone tissue, brain tissue, muscle tissue, cardiac tissue, renal tissue, liver tissue, spleen tissue, lymph tissue, eye tissue, gastrointestinal tissue, pancreatic tissue, lung tissue, kidney tissue, and/or bladder tissue. The experiments set forth, infra, in the Examples section of the present application demonstrate the ability of hyaluronidase to facilitate entry of a replacement enzyme into brain, bone, and systemic organs (e.g., kidney and liver).

As used herein, "hyaluronidase" is meant to refer to a substance which hydrolyze hyaluronic acid. Hyaluronidases suitable for use in the practice of the present invention include those described hereinabove.

Administration of the hyaluronidase to the subject can be carried out by any conventional method. Illustratively, the hyaluronidase can be administered by dissolving or suspending the hyaluronidase in a suitable carrier and administering the resulting solution or suspension enterally or parenterally (e.g., intraventricularly, intramuscularly, intravenously, intraperitoneally, rectally, subcutaneously, etc.) to the subject.

As indicated above, the method of the present invention further includes administering an enzyme to the subject.

"Enzyme", as used herein, is meant to refer to polypeptides which catalyze or are otherwise involved in biological processes. Where enzymes are employed, the choice of enzyme will typically be dictated by the disease or other condition from which the subject suffers. Enzymes suitable for use in this aspect of the present invention include those which are required normal biological function of one or more tissues, such as bone tissue, brain tissue, muscle tissue, cardiac tissue, renal tissue, liver tissue, spleen tissue, lymph tissue, eye tissue, gastrointestinal tissue, pancreatic tissue, lung tissue, kidney tissue, and/or bladder tissue. It is to be understood, that the enzyme employed in the practice of the present invention can be one which is also required for normal biological function in two such tissues, three such tissues, etc. It is to be further understood that the enzyme administered to the subject (i) can be the enzyme whose deficiency causes the disease or other condition from which the subject suffers or (ii) it can be a metabolic precursor to the enzyme whose deficiency causes the disease or other condition from which the subject suffers or (iii) it can be a modified form of the enzyme whose deficiency causes the disease or other condition from which the subject suffers, provided that the modified form of the enzyme (or its metabolic product) performs the same or substantially the same function of the enzyme whose deficiency causes the disease or other condition from which the subject. As one skilled in the art will recognize, suitable enzymes which can be administered to the subject include those of natural origin (i.e., extracted from natural sources) as well as those which have been produced synthetically or recombinantly.

Administration of the enzyme to the subject can be carried out by any conventional method. For example, the enzyme can be administered by dissolving or suspending the enzyme in a suitable carrier and administering the resulting solution or suspension enterally or parenterally (e.g., intraventricularly, intramuscularly, intravenously, intraperitoneally, rectally, subcutaneously, etc.) to the subject.

The enzyme can be administered concurrently with the hyaluronidase, either separately (e.g., in two separate suspensions or solutions, one containing the hyaluronidase and the other containing the enzyme). Alternatively, the hyaluronidase can be administered before or after the time at which the enzyme is administered, as described in greater detail hereinabove.

As indicated above, the hyaluronidase and the enzyme are administered to the subject under conditions effective to deliver the enzyme to the a tissue of the subject. As one skilled in the art will recognize, the hyaluronidase and/or enzyme may be made up, together or separately, in any suitable form appropriate for the desired use and route of administration. Examples of suitable dosage forms include oral, parenteral, or topical dosage forms and include all of the dosage forms and formulations described hereinabove. In addition to the above, generally non-active components of the above-described formulations, these formulations can include other active materials, particularly, actives which have been identified as useful in the treatment of conditions involving enzyme deficiencies or symptoms associated therewith.

It will be appreciated that the actual preferred amount of hyaluronidase and the actual preferred amount of enzyme to be administered according to the present invention will vary according to the particular enzyme, the particular composition formulated, and the mode of administration. Many factors that may modify the action of the hyaluronidase and/or of the enzyme (e.g., body weight, sex, diet, time of administration, route of administration, rate of excretion, condition of the subject, drug combinations, and reaction sensitivities and severities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests. Optimally, these factors are adjusted such that delivery of the enzyme to the subject's tissue is improved (e.g., by at least about 10%, such as by at least about 20%, by at least about 30%, by at least about 40%, and/or by at least about 50%) relative to delivery of the enzyme to the subject's tissue in the absence of hyaluronidase administration.

The present invention further relates to compositions and kits which include, at a minimum, a hyaluronidase and an enzyme which is required for a tissue's normal biological function. Suitable enzymes for use in the composition of the present invention include those which are required for normal biological function of one or more tissues selected from the group consisting of bone tissue, brain tissue, muscle tissue, cardiac tissue, renal tissue, liver tissue, spleen tissue, lymph tissue, eye tissue, gastrointestinal tissue, pancreatic tissue, lung tissue, kidney tissue, and/or bladder tissue. The compositions and kits of this aspect of the present invention can also include other active ingredients as well as non-active ingredients, such as those set forth above in connection with formulations suitable for use in methods for delivering enzymes to a tissue of a subject.

Certain aspects of the present invention are further illustrated with the following examples.

EXAMPLES

Example 1

Effect of Hyaluronidase on Evans Blue Staining of Brain Tissue

Evans Blue was used to demonstrate the action of hyaluronidase on the blood-brain barrier. Evans Blue binds to albumin when injected. The albumin is a large molecule with a high molecular weight (approximately 66 kDa) and does not cross the blood-brain barrier. Evans Blue was injected into an experimental mice, and 15 minutes thereafter, hyaluronidase was administered subcutaneously to some of the experimental mice. The following day, the mice with and without hyaluronidase were sacrificed, and the brains were examined for Evans Blue stain. Only the mice with the hyaluronidase had Evans Blue stain in the brain, indicating the albumin with Evans Blue attached to it crossed the blood-brain barrier.

Example 2

Effect of Hyaluronidase on Albumin Penetration into Brain Tissue as Demonstrated Using Anti-Albumin Antibody-Peroxidase Conjugate To further demonstrate the effect of hyaluronidase on the ability of large molecules to cross the blood brain barrier ("BBB"), uncomplexed albumin was administered to two groups of mice, one group having received hyaluronidase pretreatment (as described in Example 1) and the other having received no such pretreatment. Following administration of the albumin, the mice with and without hyaluronidase pretreatment were sacrificed, and cortex and cerebellum sections of their brains were treated with an anti-albumin antibody-peroxidase conjugate which stains albumin brown. The cortex and cerebellum sections of both groups of mice were also stained with the common microscopy stain hematoxylin/eosin, which stains glial cells blue.

Cortex sections of mice from the group which did not receive hyaluronidase pretreatment, taken 3 hours after albumin administration, showed no brown staining, and only blue-stained glia were observed.

Cortex sections of mice from the group which received hyaluronidase pretreatment, taken 3 hours after albumin administration, showed blue-stained glia and brown-stained neurons. The latter indicates that albumin had penetrated the BBB.

Cerebellum sections of mice from the group which did not receive hyaluronidase pretreatment, taken 3 hours after albumin administration, showed blue-stained glia. Several long sinuous brown structures were also observed. These brown structures are blood vessels flowing into the cerebellum and stain brown because albumin is present in the blood contained in these vessels. No brown-stained neurons were observed.

Cerebellum sections of mice from the group which received hyaluronidase pretreatment, taken 3 hours after albumin administration, showed blue-stained glia and brown-stained neurons, the latter indicating that albumin had penetrated the BBB.

Example 3

Effect of Hyaluronidase on FITC-Dextran Penetration into Various Tissues

Dextran tagged with the fluorescent dye fluorescein isothiocyanate ("FITC-Dextran") (Sigma Chemicals) was used to demonstrate the action of hyaluronidase on the blood brain barrier, on bone, and on other tissues such as kidney and liver. The dextran is a large molecule of high molecular weight (approximately 400 kDa) and does not cross the blood brain barrier or penetrate into bone.

Mice of the same age (6 months) were injected intraperitoneally ("IP") with 1000 units hyaluronidase (Sigma Chemicals), followed 15 minutes later with IP injection of 150 mg FITC-Dextran. The mice were then subjected to whole-body fluorescent imaging, using a modification of the method described in Ullberg, "The Technique of Whole-Body Autoradiography. Cryosectioning of Large Specimens," pp. 2-29 in Alvfeldt, ed., *Science Tools, Special Issue on Whole-Body Autoradiography, LKB Instrument Journal*, Bromma, Sweden: LDK Producter AB (1977), which is hereby incorporated by reference. At set intervals of 3, 6, and 24 hours, the mice were sacrificed by $CO_2$ inhalation. Carcasses were immediately immersed in a liquid hexanes-dry ice mixture at −70° C. for 5 minutes to achieve rapid freezing. Frozen carcasses were embedded in carboxymethyl cellulose gel. The carboxymethyl cellulose gel mold was again immersed in hexanes-dry ice mixture at −70° C. for 15 minutes and stored at −20° C. until the time of sectioning. Multiple sagittal sections of 10-20 micron thickness were then cut with a cryomicrotome maintained at −20° C. Sections were mounted on SCOTCH™ tape and were viewed under a UV light for fluorescein isothiocyanate ("FITC") fluorescence at 400 nm wavelength (green).

Figure 1B:
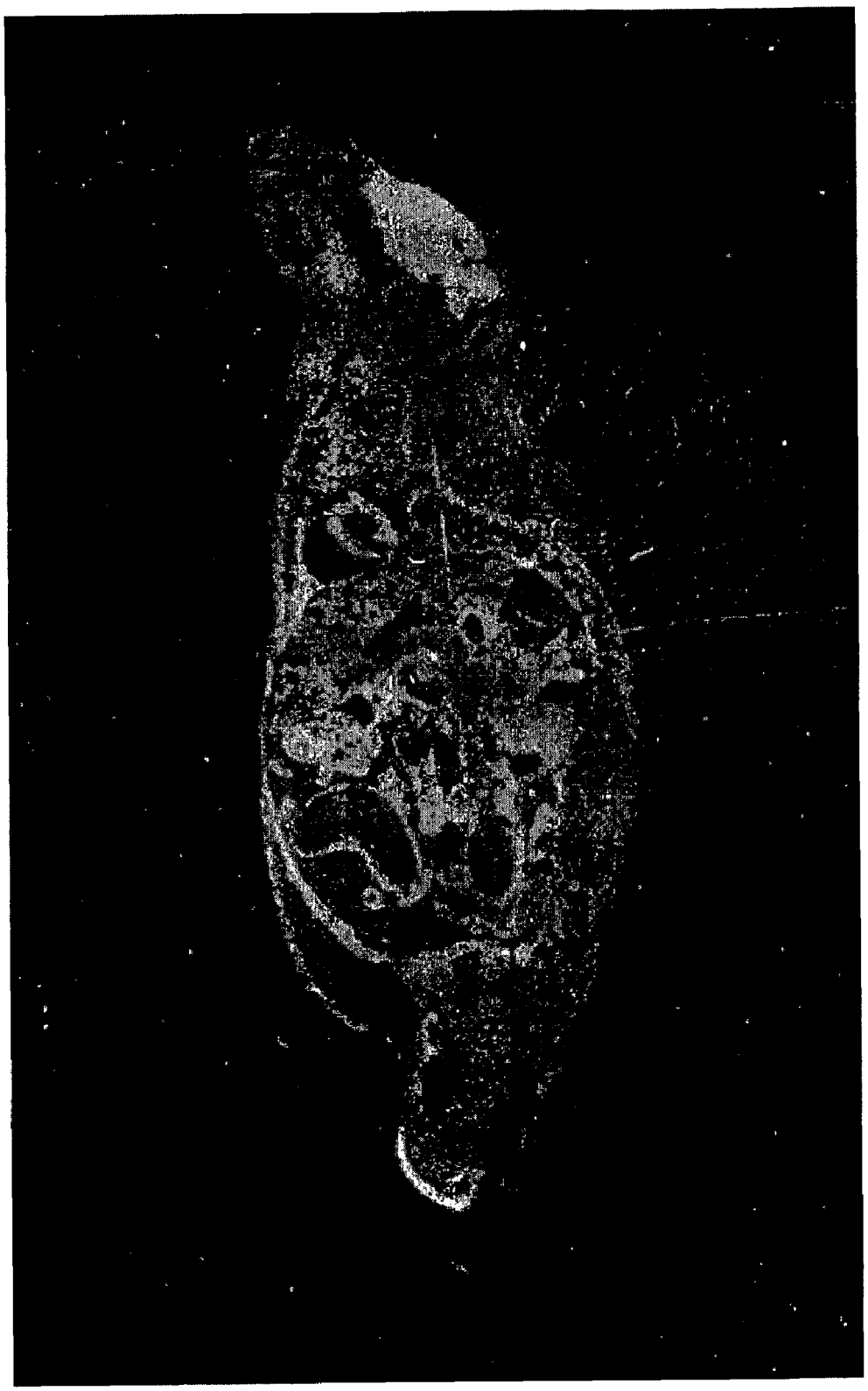
Figure 1C:
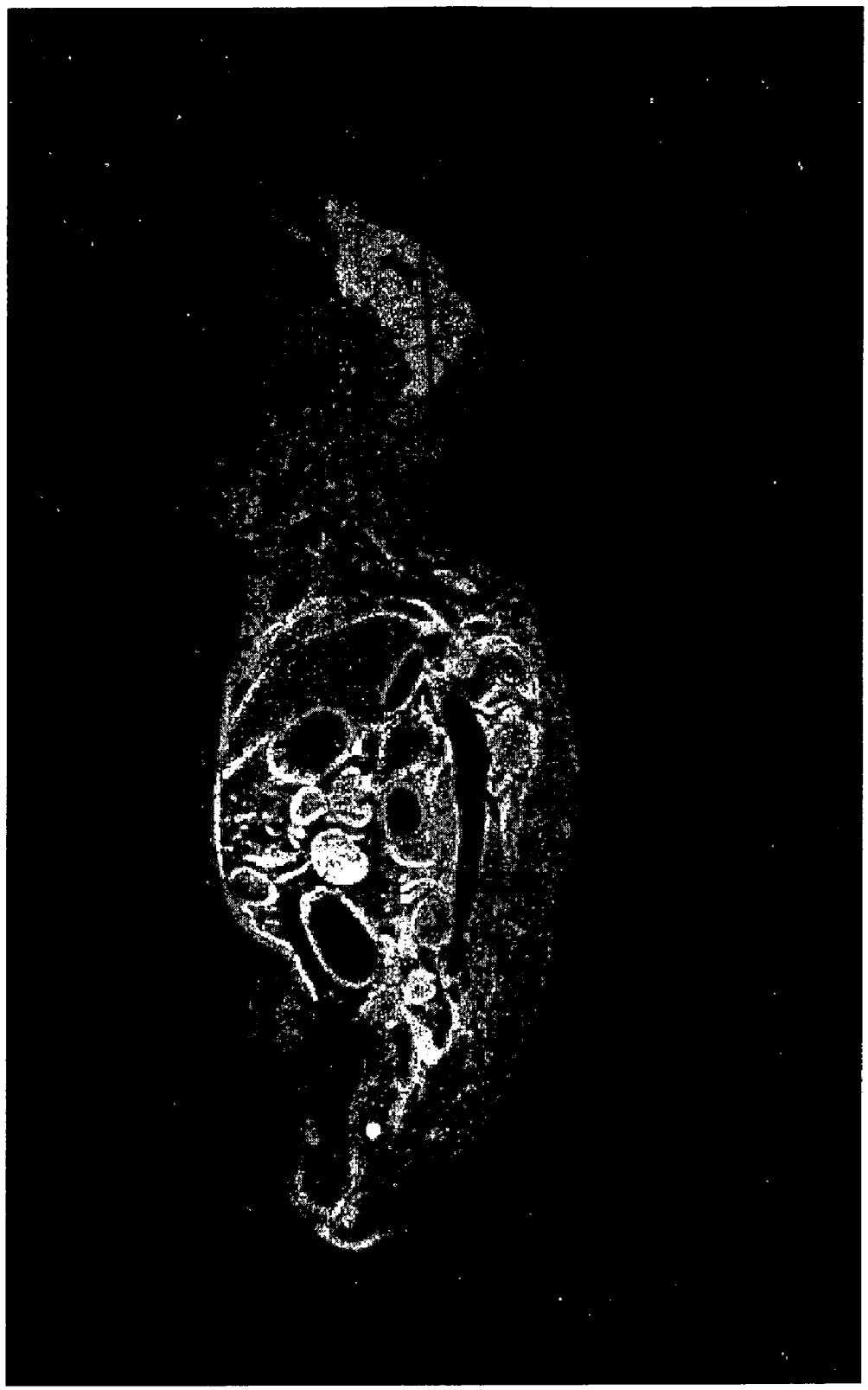

Some of the results of this experiment are presented in FIGS. 1A-1C. FIGS. 1A-1C are gray scale images of sagittal sections of mice viewed under UV light for FITC fluorescence at 400 nm wavelength. The images were recorded in color and transformed into gray scale images using color-filtering software which caused green portions of the color images to appear as bright areas in the gray scale images. FIG. 1A shows the absence of green fluorescence in a mouse to which neither FITC-Dextran nor hyaluronidase was administered, indicating that non-specific green fluorescence background is negligible. FIG. 1B shows the absence of green fluorescence in a mouse to which no hyaluronidase was administered but to which FITC-Dextran was administered. The mouse was sacrificed and the image taken, 3 hours after the FITC-Dextran administration. The absence of green fluorescence indicates that no FITC-Dextran penetration of the blood-brain barrier took place. FIG. 1C shows the green fluorescence in the brain, bone, kidney, and liver of a mouse after the administration of hyaluronidase followed 15 minutes later by FITC-Dextran administration. The mouse was sacrificed and the image taken, 3 hours after the FITC-Dextran administration. The green fluorescence indicates penetration of FITC-Dextran in the brain, bone, kidney, and liver of the mouse.

These data show that the mice to which hyaluronidase was administered exhibit increased green fluorescence that is characteristic of FITC and, thus, indicate the presence of the FITC-Dextran in the organs mentioned above. These data also show that penetration of the large molecular weight dextran into the tissues is due to the action of the hyaluronidase.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for delivering an enzyme across the blood-brain barrier to a subject's brain, said method comprising:
   administering a hyaluronidase to the subject; and
   administering an enzyme to the subject, wherein the hyaluronidase and the enzyme are administered to the subject under conditions effective to deliver the enzyme to the subject's brain.

2. A method according to claim 1, wherein the subject is a human.

3. A method according to claim 1, wherein the subject is a human suffering from a condition involving deficiency of an enzyme in the subject's brain.

4. A method according to claim 1, wherein the subject is a human having a deficiency, within the subject's brain, of an enzyme selected from the group consisting of aspartoacylase, .alpha.-galactosidase, glucocerebrosidase, sulfamidase, sphingomyelinase, .alpha.-N-acetylgalactosaminadase, and combinations thereof.

5. A method according to claim 1, wherein the subject is a human suffering from Canavan's disease, Fabry disease, Gaucher's disease, mucopolysaccharidosis, Niemann-Pick disease, Schindler disease, or combination thereof.

6. A method according to claim 1, wherein the subject is a human suffering from Canavan's disease, Fabry disease, Gaucher's disease, Sanfillippo A syndrome, Hurler's syndrome, Hurler-Sheie syndrome, Niemann-Pick disease, Schindler disease, or combinations thereof.

7. A method according to claim 1, wherein the enzyme is selected from the group consisting of aspartoacylase, .alpha.-galactosidase, glucocerebrosidase, sulfamidase, sphingomyelinase, and .alpha.-N-acetylgalactosaminadase.

8. A method according to claim 1, wherein the subject is a human having an .alpha.-galactosidase deficiency within the subject's brain; and wherein the enzyme is an .alpha.-galactosidase.

9. A method according to claim 1, wherein the subject is a human having an aspartoacylase deficiency.

10. A method according to claim 1, wherein the hyaluronidase is administered to the subject after administering the enzyme to the subject.

11. A method according to claim 1, wherein the hyaluronidase and the enzyme are simultaneously administered to the subject.

12. A method according to claim 1, wherein the hyaluronidase is administered to the subject prior to administering the enzyme to the subject.

13. A method according to claim 1, wherein the hyaluronidase is administered to the subject, in a single dose, prior to administering the enzyme to the subject.

14. A method according to claim 1, wherein the hyaluronidase is administered to the subject after administering the enzyme to the subject; simultaneously with administering the enzyme to the subject; and/or in a single dose, in multiple doses, or continuously within a 24-hour period immediately preceding administration of the enzyme to the subject.

15. A method according to claim 1, wherein the subject is a human and wherein the hyaluronidase is administered to the subject prior to administering the enzyme to the subject.

* * * * *